United States Patent
Kajihara

(10) Patent No.: US 8,119,982 B2
(45) Date of Patent: Feb. 21, 2012

(54) METHOD AND SYSTEM FOR MASS SPECTROMETRY DATA ANALYSIS

(75) Inventor: Shigeki Kajihara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 323 days.

(21) Appl. No.: 12/594,480

(22) PCT Filed: Apr. 4, 2007

(86) PCT No.: PCT/JP2007/000366
§ 371 (c)(1),
(2), (4) Date: Oct. 2, 2009

(87) PCT Pub. No.: WO2008/126151
PCT Pub. Date: Oct. 23, 2008

(65) Prior Publication Data
US 2010/0116981 A1    May 13, 2010

(51) Int. Cl.
*H01J 49/26* (2006.01)
*B01D 59/44* (2006.01)

(52) U.S. Cl. ............... 250/282; 250/281; 702/28
(58) Field of Classification Search ............ 250/281, 250/282; 702/19, 23, 27–28
See application file for complete search history.

(56) References Cited

U.S. PATENT DOCUMENTS

| | | | |
|---|---|---|---|
| 5,808,300 A * | 9/1998 | Caprioli | 250/288 |
| 2007/0042496 A1* | 2/2007 | Okamoto et al. | 436/86 |
| 2009/0159789 A1* | 6/2009 | Yamaguchi | 250/281 |
| 2009/0272890 A1* | 11/2009 | Ogawa et al. | 250/281 |

FOREIGN PATENT DOCUMENTS

| | | |
|---|---|---|
| JP | 2006-010658 A | 1/2006 |
| JP | 2006-284509 A | 10/2006 |
| WO | 2005/003715 A2 | 1/2005 |

OTHER PUBLICATIONS

Satoka Aoyagi, "Time-of-Flight Secondary Ion Mass Spectrometry Imaging of Biodevices", J. Mass Spectrom Soc. Jpn., Feb. 1, 2007, pp. 33-38, vol. 55, No. 1.

(Continued)

*Primary Examiner* — Jack Berman
*Assistant Examiner* — David E Smith
(74) *Attorney, Agent, or Firm* — Sughrue Mion, PLLC

(57) ABSTRACT

In the process of identifying a protein by analyzing and processing mass spectrum data obtained for each micro area (pixel) created by subdividing a two-dimensional area on a sample, mass windows including a peak or peaks on the mass spectrum of each pixel are set (S10), and an integrated value of the ion intensities of the peaks included in each mass window is calculated (S11). For each mass window, a mapping image is created by collecting the integrated intensity values of the pixels (S12), and the mass windows are grouped by evaluating the similarity of the mapping images (S13 and S14). The peaks included in the mass windows belonging to the same group are regarded as originating from the same kind of substance, and those peaks are collected to create a mass spectrum (S15). Based on this spectrum, a protein is identified by a PMF method or the like. The present method can achieve a high level of identifying accuracy even if two or more kinds of proteins are mixed together.

7 Claims, 8 Drawing Sheets

OTHER PUBLICATIONS

Timothy J. Garrett, et al., "Imaging of small molecules in tissue sections with a new intermediate-pressure MALDI linear ion trap mass spectrometer", International Journal of Mass Spectrometry, Feb. 1, 2007, pp. 166-176, vol. 260, No. 2-3.

Katrin Börner, et al., "Molecular imaging of lipids in cells and tissues", International Journal of Mass Spectrometry, Feb. 1, 2007, pp. 128-136, vol. 260 No. 2-3.

Ioana M. Taban, et al., "Imaging of Peptides in the Rat Brain Using MALDI-FTICR Mass Spectrometry", Journal of the American Society for Mass Spectrometry, Jan. 2007, pp. 145-151, vol. 18, No. 1.

Kiyoshi Ogawa, et al., "Research and Development of Mass Microscope", Shimadzu Review, Mar. 31, 2006, pp. 125-135, vol. 62, No. 3/4.

Yasuhide Naito, "Mass Microprobe Aimed at Biological Samples", J. Mass Spectrom, Soc. Jpn., 2005, pp. 125-132, vol. 53, No. 3.

* cited by examiner

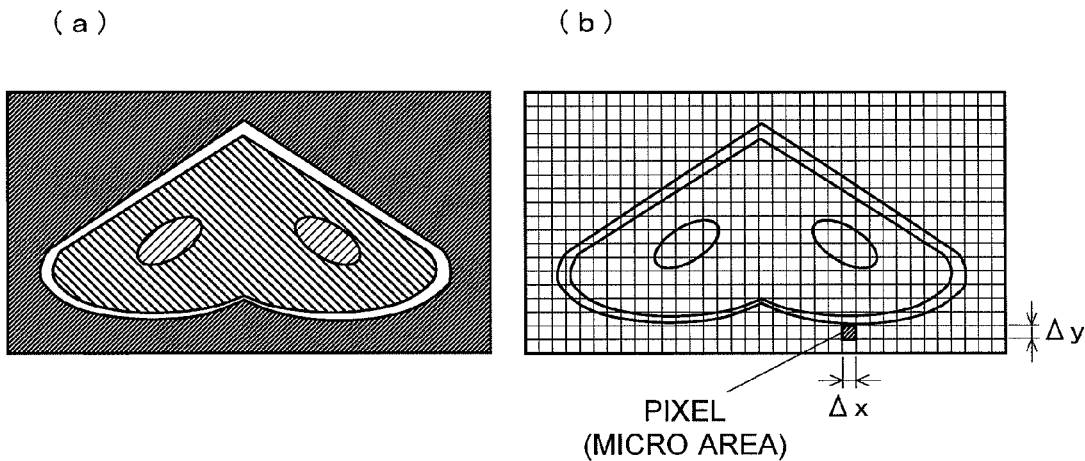

PIXEL (MICRO AREA)   Δx   Δy

Fig. 4

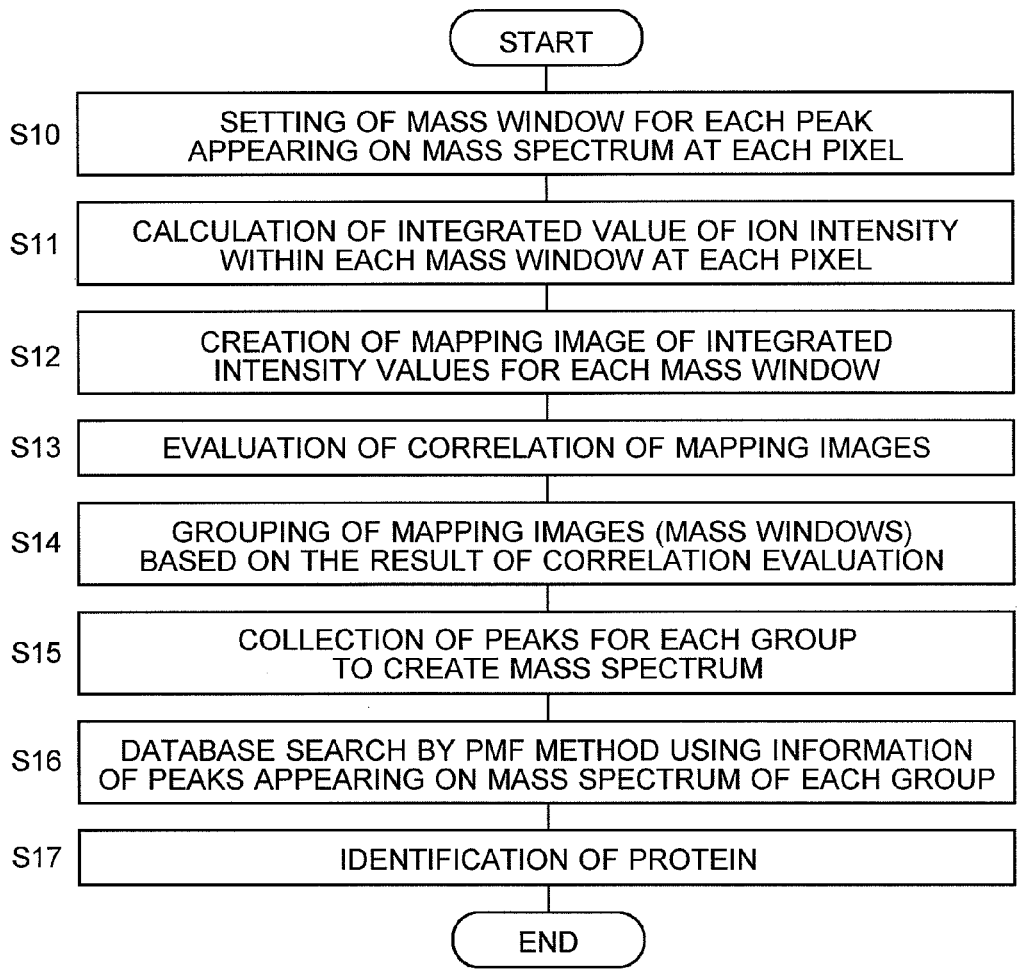

- S10: SETTING OF MASS WINDOW FOR EACH PEAK APPEARING ON MASS SPECTRUM AT EACH PIXEL
- S11: CALCULATION OF INTEGRATED VALUE OF ION INTENSITY WITHIN EACH MASS WINDOW AT EACH PIXEL
- S12: CREATION OF MAPPING IMAGE OF INTEGRATED INTENSITY VALUES FOR EACH MASS WINDOW
- S13: EVALUATION OF CORRELATION OF MAPPING IMAGES
- S14: GROUPING OF MAPPING IMAGES (MASS WINDOWS) BASED ON THE RESULT OF CORRELATION EVALUATION
- S15: COLLECTION OF PEAKS FOR EACH GROUP TO CREATE MASS SPECTRUM
- S16: DATABASE SEARCH BY PMF METHOD USING INFORMATION OF PEAKS APPEARING ON MASS SPECTRUM OF EACH GROUP
- S17: IDENTIFICATION OF PROTEIN

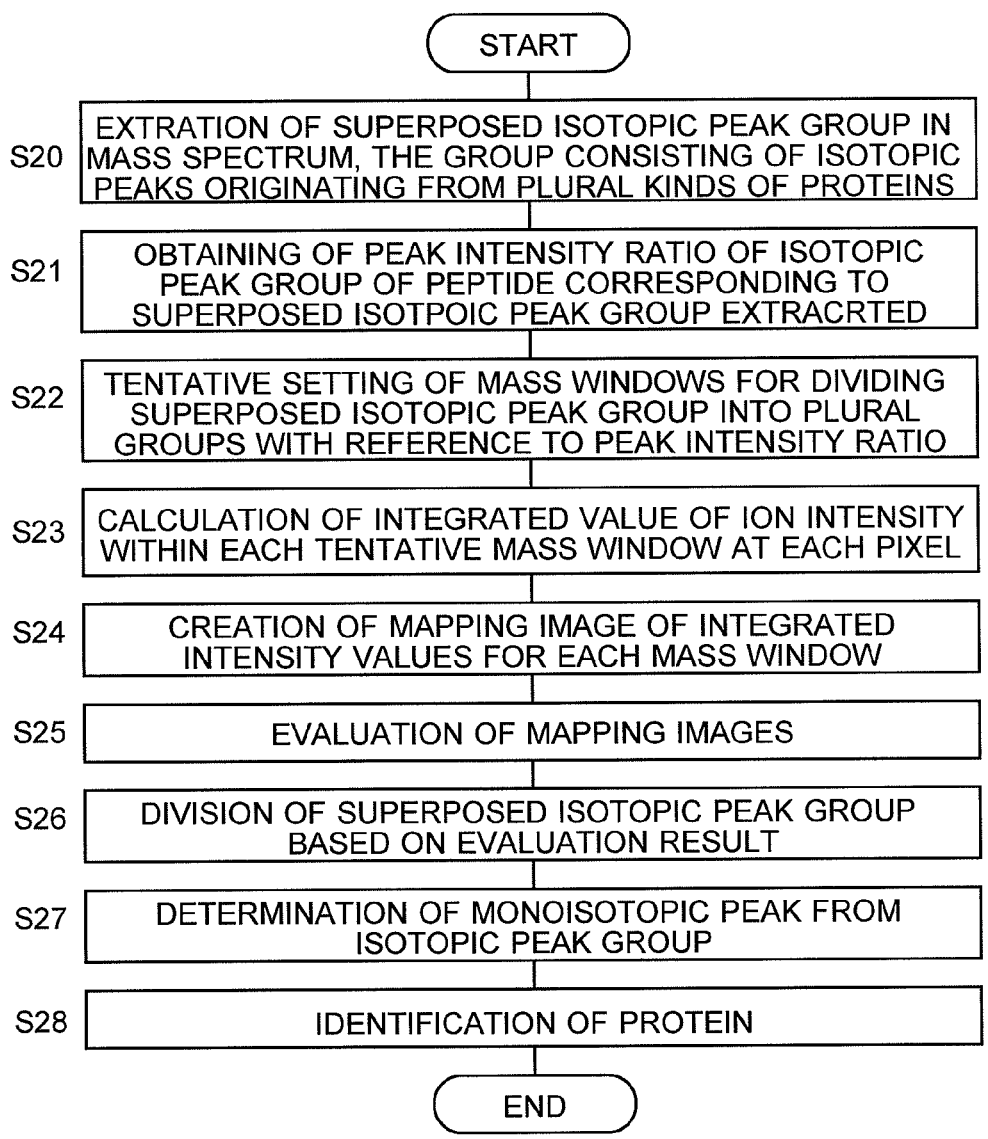
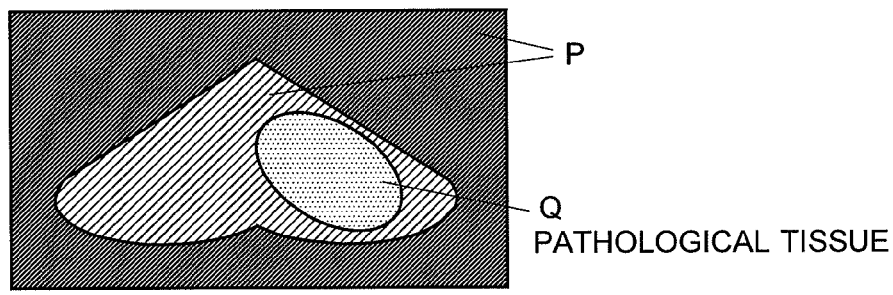

METHOD AND SYSTEM FOR MASS SPECTROMETRY DATA ANALYSIS

TECHNICAL FIELD

The present invention relates to a method and system for mass spectrometry data analysis for analyzing and processing mass spectrum data collected for each micro area of a two-dimensional area on a sample. More specifically, it relates to a method and system for mass spectrometry data analysis suitable for identifying proteins or other substances contained in a sample originating from a living organism.

BACKGROUND ART

In recent years, structural and functional analyses of proteins in living tissues have been rapidly promoted as the post-genome research. For such structural and functional analyses of proteins (proteome analysis), the methods that have involved using a mass spectrometer for the expression analysis or primary structure analysis of a protein have been widely used in recent years. A conventional example of this kind of method is called a peptide mass fingerprinting (PMF). This method includes extraction of a protein from a sample, followed by the purification and separation of that protein by two-dimensional electrophoresis or other techniques. The separated protein is then digested with an appropriate enzyme to form a mixture of peptide fragments, and the mass of each fragmentary peptide is precisely measured by a matrix-assisted laser desorption ionization time-of-flight mass spectrometer (MALDI-TOFMS) or other apparatuses. Subsequently, a database search using a search engine is performed to locate a protein containing a peptide whose mass matches the measured mass data. Eventually, a list of probable candidates of the protein is shown as an identification result.

A mass spectrometer capable of MS/MS analysis (or tandem analysis), which captures and dissociates a specific peak by a quadrupole ion trap, collision-induced dissociation (CID) and other techniques, can also be used to determine the amino acid sequence of a protein as follows: The protein is initially digested with an appropriate enzyme to form a mixture of peptide fragments. This peptide mixture is then subjected to mass analysis. The constituent elements of each peptide have stable isotopes having different masses. Therefore, even if one peptide has the same amino acid sequence as that of another, these peptides will have peaks at different mass-to-charge ratios due to the difference in their isotopic composition. The resultant peaks include the peak of an ion that has no isotopic element (mono-isotopic ions) and those of the other ions that contain isotopic elements (isotopic ions). These peaks form a peak group in which a plurality of peaks are located at intervals of 1 Da (in the case of a monovalent ion). (This group is hereafter called an isotopic peak group.)

Subsequently, one isotopic peak group originating from the same peptide is entirely (or partially in some cases) selected as a precursor ion from the mass spectrum data of the peptide mixture. This precursor ion is then dissociated into smaller ions (product ions), which in turn are subjected to mass analysis (MS/MS analysis). Based on the pattern of the mass spectrum of the product ions obtained in this manner and/or the pattern of the mass spectrum of the precursor ion, a database search is conducted to determine the amino acid sequence of the peptide in question and identify the protein (refer to Patent Document 1 and other references).

The previously described protein identification technique basically premises the extraction of proteins from a cell or other specimen, followed by the purification and separation of the proteins to prepare a sample to be analyzed. However, in biochemical, medical and other technical fields, there is a strong demand for the acquisition of information relating to a two-dimensional protein distribution within an in-vivo cell without breaking the cell. To fulfill this requirement, a mass microscope having the functions of both a microscope and a mass spectrometer has been under development. (A mass microscope may also be called an imaging mass spectrometer). With an imaging mass spectrometer, it is possible to obtain distribution information (e.g. a mapping image) of a substance within a two-dimensional area on a sample placed on a preparation or other locations. To date, various configurations have been proposed for the acquisition of mass spectrum data for each micro area within a two-dimensional area on a sample in an imaging mass spectrometer.

For example, the mass spectrometer disclosed in Patent Document 2 or Non-Patent Document 1 scans the surface of a sample by sequentially moving the irradiation point of a laser beam or particle beam for ionization; every time the irradiation point is moved, the ions generated from the irradiation point are individually detected with respect to their mass. According to the method proposed in Non-Patent Document 2, ions are almost simultaneously generated over a two-dimensional area of a sample so that they will reflect the two-dimensional distribution of the substances on the sample; those ions are then mass-separated by a time-of-flight mass separator and detected by a two-dimensional detector.

In any of these techniques, creation of a mapping image of a substance within a two-dimensional area on a sample requires analyzing and processing mass spectrum data obtained for each micro area within the two-dimensional area and specifying a substance (e.g. a protein) present in each micro area. In the case of a mass spectrometer capable of MS/MS analysis (or tandem analysis), mass spectrum data obtained by a mass analysis without dissociation of ions is initially analyzed to specify an ion to be selected as a precursor ion. After an appropriate precursor ion is selected for each micro area, an MS/MS analysis is carried out to obtain mass spectrum data for each micro area, and these data are analyzed to identify a substance present in each micro area.

However, it is difficult to identify a protein within a micro area on a sample on the basis of mass spectrum data obtained for that area. A major reason is because there are often two or more kinds of proteins within one micro area if the sample is a portion of a living tissue. In the case of the aforementioned protein identification technique, it is least possible for peaks originating from different proteins to overlap each other on a mass spectrum since each protein contained in an analyte is purified and separated beforehand by a preprocess. On the other hand, performing a mass analysis of a sample with two or more kinds of proteins mixed together allows peaks originating from different proteins to be mixed together on the mass spectrum. In this state, it is impossible to correctly identify each protein by referencing a database prepared for the deduction of amino acid sequences. Another problem with this type of mass spectrum exists in that locating an isotopic peak group in the previously described manner is difficult since two or more isotopic peak groups originating from different proteins are often overlapped with each other, making it difficult to correctly identify the peaks belonging to a specific isotopic peak group by simply checking their peak intensity ratio. This results in a decrease in the identification accuracy since a set of peaks originating from the same substance cannot be correctly selected as a precursor ion for the MS/MS analysis.

Patent Document 1: Japanese Unexamined Patent Application Publication No. 2006-284509

Patent Document 2: U.S. Pat. No. 5,808,300

Non-Patent Document 1: Kiyoshi Ogawa et al., "Kenbi Shisuryou Bunseki Souchi No Kaihatsu (Research Development of Mass Microscope)", *Shimadzu Hyouron (Shimadzu Review)*, Shimadzu Hyouron Henshuu-bu, Mar. 31, 2006, Vol. 62, No. 3/4, pp. 125-135

Non-Patent Document 2: Yasuhide Naito, "Seitai Shiryou Wo Taishou Ni shia Shitsuryou Kenbikyou (Mass Microprobe Aimed at Biological Samples), Journal of the Mass Spectrometry Society of Japan Vo. 53 (2005), No. 3

DISCLOSURE OF THE INVENTION

Problem to be Solved by the Invention

The present invention has been developed to solve these problems. Thus, in a method and system for mass spectrometry data analysis for creating, for example, a substance distribution image of a two-dimensional area on a sample by using mass spectrum data obtained by mass analysis for each micro area of the two-dimensional area, the present invention is aimed at providing a method and system that can identify a substance and determine its quantity with higher levels of accuracy and hence is capable of creating more correct substance distribution images.

Means for Solving the Problem

The previously described mass microscope (or imaging mass spectrometer) can obtain not only mass spectrum data (i.e. two-dimensional information showing the mass and peak intensity) for each micro area but also the spatial information of each peak (i.e. two-dimensional information showing the position of each peak in the x-direction and y-direction which is orthogonal to the x-direction). However, the spatial distribution information has not been used to determine whether a set of peaks have originated from the same substance. The present invention utilizes this spatial information in addition to the mass spectrum, i.e. a total of four pieces of information to distinguish the peaks originating from the same substance from a mixture of peaks that have originated from two or more substances.

Thus, a first aspect of the present invention aimed at solving the aforementioned problems provides a mass spectrometry data analysis method for analyzing and processing mass spectrum data collected by a mass analysis performed for each of the micro areas defined within a predetermined two-dimensional area on a sample, which is characterized by including a distinguishing step for distinguishing a peak or peak set originating from one kind of substance from a peak or peak set originating from another kind of substance, using a two-dimensional distribution of a peak having the same mass and appearing on mass spectrums corresponding to a portion or the entirety of the micro areas or a peak set composed of one or more peaks included in the same mass range on the mass spectrums.

A second aspect of the present invention, which is one mode of the mass spectrometry data analysis method according to the first aspect of the present invention, is a mass spectrometry data analysis method for analyzing and processing mass spectrum data collected by performing a mass analysis for each of the micro areas defined within a predetermined two-dimensional area on a sample, which is characterized by including:

a) a distribution determining step for determining a two-dimensional distribution of each peak having the same mass and appearing on mass spectrums corresponding to a portion or the entirety of the micro areas or each peak set composed of one or more peaks included in the same mass range on the mass spectrums;

b) a grouping step for separating the peaks or peak sets into one or more groups based on a degree of similarity of the two-dimensional distribution; and c) a spectrum creating step for creating a mass spectrum for each group from the peaks or peak sets separated into the group, and an identification process is performed on the assumption that the mass spectrum created in the spectrum creating step has originated from the same substance.

A third aspect of the present invention aimed at solving the aforementioned problems is a system embodying the mass spectrometry data analysis method according to the second aspect of the present invention and is characterized by including:

a) a distribution determining means for determining a two-dimensional distribution of each peak having the same mass and appearing on mass spectrums corresponding to a portion or the entirety of the micro areas or each peak set composed of one or more peaks included in the same mass range on the mass spectrums;

b) a grouping means for separating the peaks or peak sets into one or more groups based on the degree of similarity of the two-dimensional distribution;

c) a spectrum creating means for creating a mass spectrum for each group from the peaks or peak sets classified into the group; and d) an identifying means for performing an identification process on the assumption that the mass spectrum created by the spectrum creating means has originated from the same substance.

The "peak set composed of one or more peaks included in the same mass range" may be, for example, a single peak whose intensity value is defined as an integrated value of the intensities of two or more peaks located within a mass window having a predetermined mass width on a mass spectrum.

For example, in an analysis of a biological sample, a plurality of peaks originating from the same kind of protein (i.e. peaks of peptides) appear on the mass spectrum. If there are two or more kinds of proteins within a micro area of the mass analysis target, the peaks originating from these two or more kinds of proteins will be mixed together on the mass spectrum, making it difficult to determine which of those peaks have originated from the same kind of protein. However, if the entire two-dimensional area of the sample is investigated, the peaks that have originated from the same kind of protein should have the same distribution pattern. Accordingly, for example, the two-dimensional distribution of a peak set included in the same mass range and appearing on the mass spectrums corresponding to the entirety of micro areas is determined in the distribution determining step, to create a mapping image showing the distribution of the peak set for each mass range. Thus, as many mapping image as the number of specified mass ranges are created.

The grouping step involves, for example, the checking of the similarity of the mapping images, followed by the grouping of apparently similar mapping images (i.e. the peaks or peak sets, or masses or mass ranges, from which the mapping images have been created) into the same group. Any peak that is unmistakably considered to be a noise peak should be excluded. It is most likely that the peaks or peak sets classified into the same group have originated from the same kind of protein. Accordingly, in the spectrum creating step, a mass spectrum is newly created for each group by collecting the peaks or peak sets included in the group concerned. Thus, as many mass spectra as the number of groups are created. Then, on the assumption that each of these mass spectrums has originated from the same kind of protein, an identification process for each protein is performed. The identification process can be performed by conventional methods, such as the previously explained PMF method.

A fourth aspect of the present invention, which is another mode of the mass spectrometry data analysis method according to the first aspect of the present invention, is a mass spectrometry data analysis method for analyzing and processing mass spectrum data collected by performing a mass analysis for each of the micro areas defined within a predetermined two-dimensional area on a sample, which is characterized by including:

a) an isotopic group extracting step for extracting a superposed isotopic peak group formed by a plurality of isotopic peak groups originating from two or more kinds of substances and superposed on each other on a mass spectrum corresponding to one of the micro areas;

b) a separation candidate calculating step for finding a candidate combination of the peaks for separating the superposed isotopic peak group into individual isotopic peak groups each originating from one kind of substance, by using a theoretical peak intensity ratio deduced from the mass of a specific peak selected from a plurality of peaks composing the superposed isotopic peak group;

c) a distribution determining step for setting a mass range including a peak belonging to an isotopic peak group for each candidate combination of the peaks, and for determining a two-dimensional distribution of each peak set composed of one or more peaks included in the aforementioned mass range and appearing on the mass spectrums corresponding to a portion or the entirety of the micro areas; and d) an isotopic peak group separating step for separating the superposed isotopic peak group into individual isotopic peak groups by selecting one candidate of the peak combination on the basis of the aforementioned two-dimensional distribution.

A fifth aspect of the present invention aimed at solving the aforementioned problem is a system embodying the mass spectrometry data analysis method according to the fourth aspect of the present invention and is characterized by including:

a) an isotopic group extracting means for extracting a superposed isotopic peak group resulting from a plurality of isotopic peak groups originating from two or more kinds of substances and superposed on each other on a mass spectrum corresponding to one of the micro areas;

b) a separation candidate calculating means for finding a candidate combination of the peaks for separating the superposed isotopic peak group into individual isotopic peak groups each originating from one kind of substance, by using a theoretical peak intensity ratio deduced from the mass of a specific peak selected from a plurality of peaks composing the superposed isotopic peak group;

c) a distribution determining means for setting a mass range including a peak belonging to an isotopic peak group for each candidate combination of the peaks, and for determining a two-dimensional distribution of each peak set composed of one or more peaks included in the aforementioned mass range and appearing on the mass spectrums corresponding to a portion or the entirety of the micro areas; and d) an isotopic peak group separating means for separating the superposed isotopic peak group into individual isotopic peak groups by selecting one candidate of the peak combination on the basis of the aforementioned two-dimensional distribution.

The mass spectrometry data analysis method according to the fourth aspect of the present invention pays particular attention to a superposed isotopic peak group, which is a mixture of peaks originating from two or more kinds of substances (which are typically proteins) on a mass spectrum; this method uses distribution information covering the entire two-dimensional area of the sample to determine which peaks belong to each of the plural isotopic peak groups that compose the superposed isotopic peak group. For this purpose, the distribution determining step includes, for example, the creation of a mapping image that shows the two-dimensional distribution of an isotopic peak group for each candidate of the peak combination computed in the candidate separation calculating step. If, for example, the superposed isotopic peak group being analyzed is located on a mass spectrum corresponding to a micro area belonging to a specific portion of the two-dimensional area of a sample that can be unmistakably distinguished from the other portions by visual observation with a normal microscope or other devices, then the mapping image should be an image on which the specific portion is distinguishable from the other portions if the isotopic peak groups are correctly separated. Accordingly, in the isotopic peak group separating step, the mapping image created by the previous step is evaluated, for example, by comparison to another image observed with a normal microscope, to determine which method of separation of the isotopic peak groups is appropriate.

After the isotopic peak groups have been thus established, it is possible, for example, to locate a mono-isotopic peak and perform a database search using the located peak to identify a protein. Alternatively, the separated isotopic peak group may be entirely or partially used as a precursor ion to perform an MS/MS analysis and identify the protein based on the mass spectrum data obtained by the MS/MS analysis.

Effect of the Invention

According to the methods and systems for mass spectrometry data analysis according to the first through fifth aspects of the present invention, even if there are two or more kinds of substances within a two-dimensional area on a sample, it is possible to accurately identify each substance. Based on this identification result or the result of a quantitative analysis of each of the identified substances, it is possible to create a correct mapping image for each substance within the two-dimensional area.

BRIEF DESCRIPTION OF THE DRAWINGS

FIG. 3 is a diagram for illustrating the operation of collecting mass spectrum data by the mass spectrometer shown in FIG. 1 or 2.

FIG. 4 is a flowchart showing the process steps of a mass spectrometry data analysis method according to the first embodiment of the present invention.

FIG. 7 is a flowchart showing the process steps of a mass spectrometry data analysis method according to the second embodiment of the present invention.

FIG. 8 is a diagram showing one example of a sample to be analyzed by the mass spectrometry data analysis method according to the second embodiment.

EXPLANATION OF NUMERALS

2 . . . Sample Stage
3 . . . Stage Drive Unit
4 . . . Laser Unit
5, 11 . . . Ion Transport Optical System
6 . . . Mass Analyzer
7 . . . Ion Detector
8, 15 . . . Data Processing Unit
10 . . . Laser Beam
13 . . . Magnifying Ion Optical System
14 . . . Two-Dimensional Ion Detector

BEST MODE FOR CARRYING OUT THE INVENTION

Examples of the configuration of a mass spectrometer for collecting mass spectrum data to be analyzed and processed by a method and system for mass spectrometry data analysis according to the present invention are initially described in this section.

Figure 1:
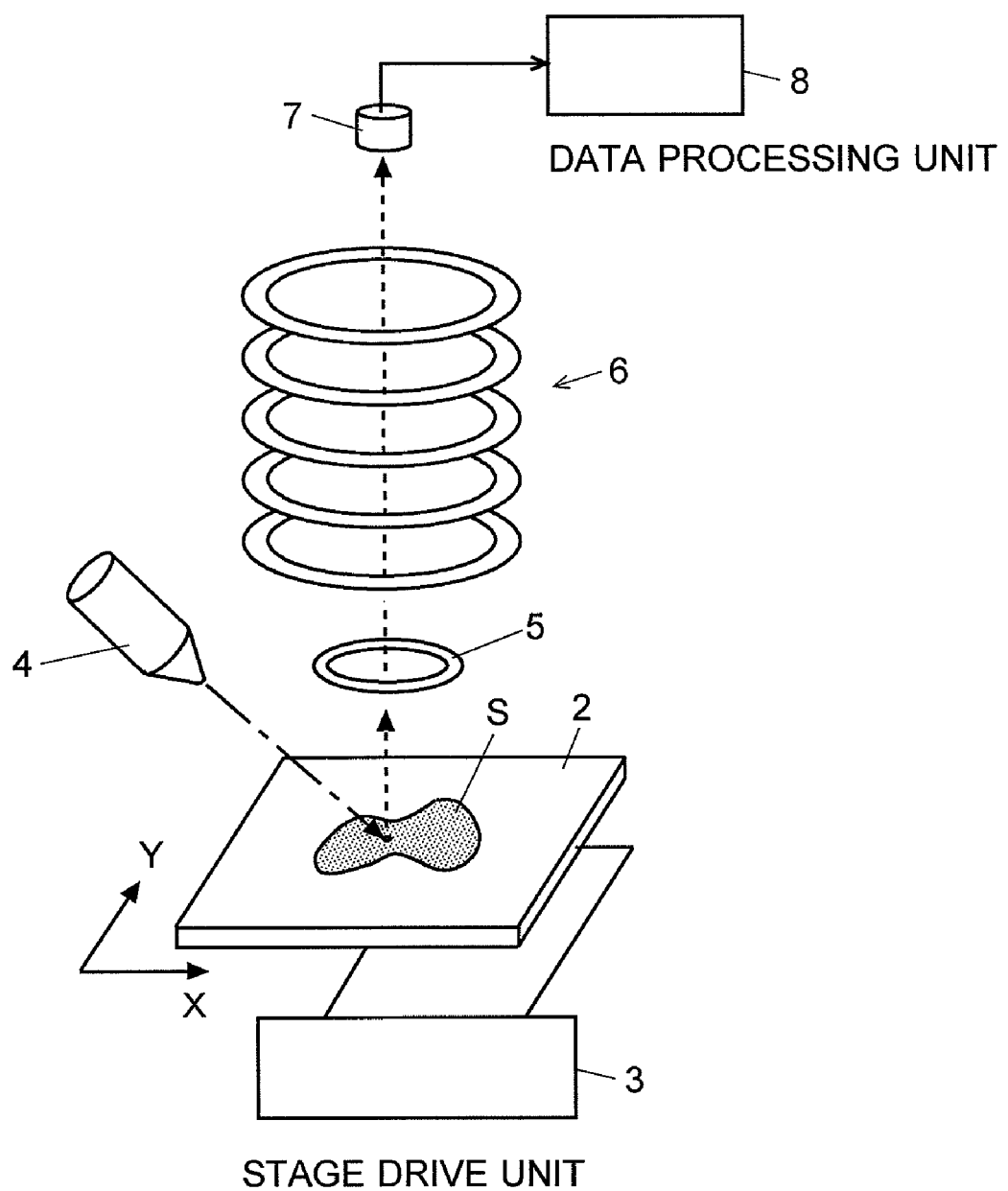
FIG. 1 is a schematic configuration diagram showing an embodiment of a mass spectrometer for collecting mass spectrum data to be analyzed and processed by a method and system for mass spectrometry data analysis according to the present invention.

FIG. 1 is a schematic configuration diagram of the mass spectrometer according to one embodiment. In this mass spectrometer, a sample stage 2, on which a sample S to be analyzed is placed, can be moved by a stage drive unit 3 across a predetermined range in each of the X and Y directions orthogonally intersecting each other in FIG. 1. When a laser beam with a micro-sized diameter is delivered from a laser unit 4 onto the sample S, various kinds of molecules on the irradiated portion are vaporized and ionized. The ions emitted from the sample S are captured by an ion transport optical system 5 and introduced into a mass analyzer 6 in the subsequent stage. An example of the mass analyzer 6 is a time-of-flight mass analyzer, in which case the introduced ions pass through the mass analyzer 6 with a time of flight corresponding to their mass (specifically, their mass-to-charge ratio: m/z) and reach an ion detector 7. The ion detector 7 produces a detection signal corresponding to the amount of incoming ions, and this signal is sent to a data processing unit 8. The data processing unit 8 converts the detection signal into digital values and the time-of-flight into the mass axis, to determine the intensity data with respect to each mass. Thus, mass spectrum data are obtained. These data are then plotted on a graph with m/z on the horizontal axis and the (relative) intensity of the ions on the vertical axis to create a mass spectrum.

The portion on the sample S that can be mass-analyzed by a single laser-irradiating operation is an extremely small (micro-sized) area illuminated by the laser beam. Accordingly, the sample stage 2 is stepwisely moved by the stage drive unit 3 in the X and Y directions in a predetermined order. For each position of the stage 2, the laser beam is delivered onto the sample and the mass analysis is performed as described previously to obtain detection signals. Thus, mass spectrum data can be collected for each micro area defined within a predetermined two-dimensional area on the sample S. Though not shown, the mass spectrometer is provided with a microscope for optically observing the surface of the sample S or an imaging system including a CCD camera or similar device for taking a two-dimensional image of the sample S and a monitor for showing the image. Based on this observed image, users can arbitrarily set a two-dimensional area on which the mass analysis is to be performed.

For example, if the sample S is a sliced portion of a mouse's brain, a two-dimensional observation image will be obtained as shown in FIG. 3(a). Then, as shown in FIG. 3(b), micro areas are defined by dividing the two-dimensional area in a grid pattern with mesh sizes of $\Delta x$ and $\Delta y$ in the X and Y directions, respectively. That is, each micro area has a size of $\Delta x \times \Delta y$, and the aforementioned mass spectrum is obtained for each area with this size. Although the previous description assumed that the location of the mass analysis was changed by moving the sample stage 2 with the laser irradiation point fixed, it is alternatively possible to move the laser irradiation point with the sample stage 2 fixed. However, the latter method causes a change in the absolute position of the portion from which ions are generated. Therefore, it is preferable to move the ion transport system 5 and mass analyzer 6 in synchronization with the laser irradiation point so as to efficiently collect the generated ions.

Figure 2:
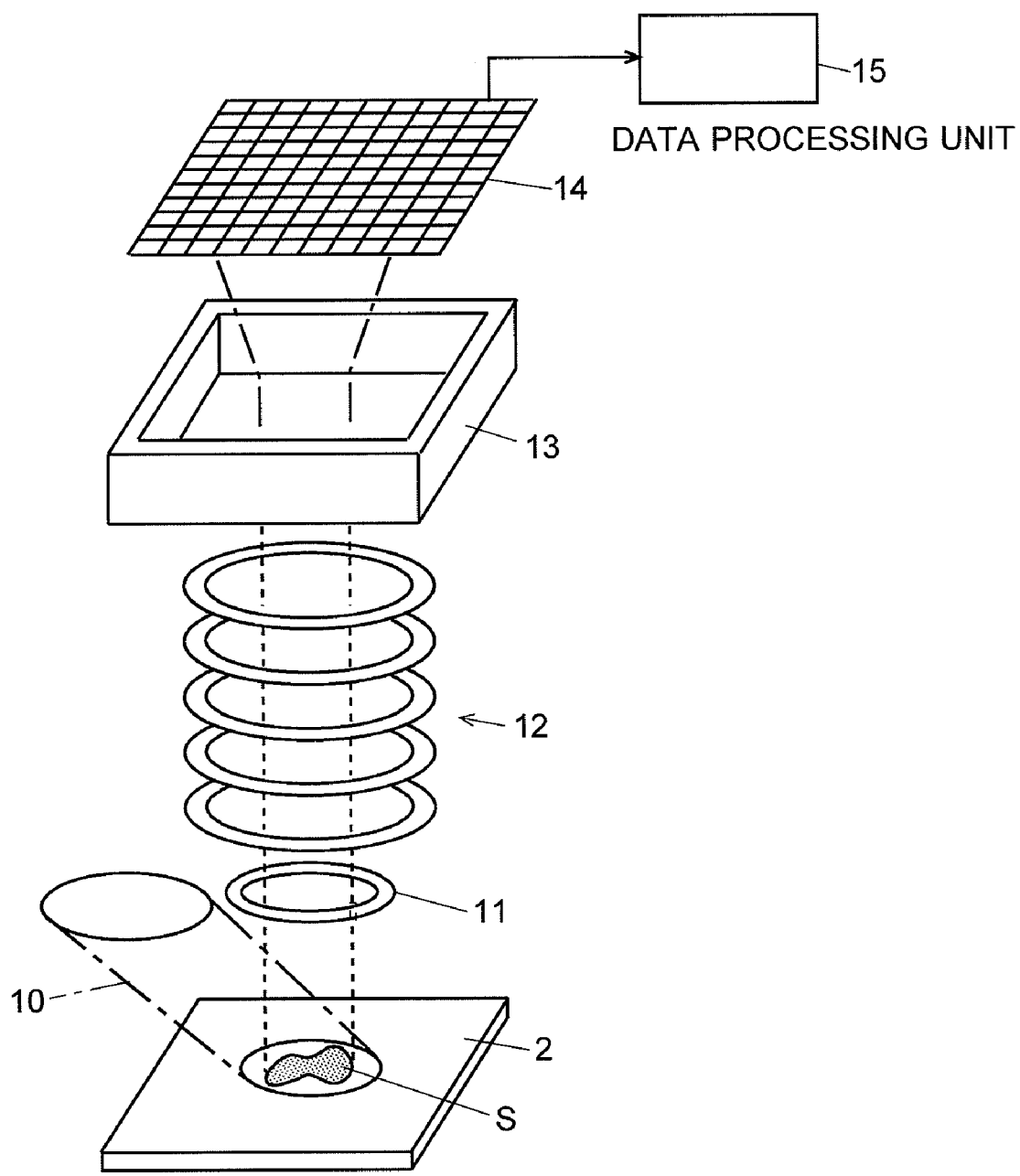
FIG. 2 is a schematic configuration diagram showing another embodiment of a mass spectrometer for collecting mass spectrum data to be analyzed and processed by a method and system for mass spectrometry data analysis according to the present invention.

FIG. 2 is a schematic configuration diagram of a mass spectrometer according to another embodiment. In this embodiment, a two-dimensionally spread laser beam 10 is delivered onto a sample S placed on the sample stage 2. Irradiation of the sample S with this laser beam 10 simultaneously causes ionization at every point within a two-dimensional area on the sample S. The generated ions are introduced into a mass analyzer 12 through an ion transport optical system 11, which is capable of maintaining the relative relationship of the original positions of the ions. The mass analyzer 12 separates the ions with respect to their mass, while maintaining the relative relationship of the original positions of the ions. The separated ions are then introduced through a magnifying ion optical system 13 into a two-dimensional ion detector 14 with a two-dimensional array of micro-sized ion detectors. This means that the two-dimensional ion detector 14 detects the ions generated from the two-dimensional area of the sample S while preserving the information indicative of the original positions of the ions. A data processing unit 15 converts the incoming detection signals into digital values and separates the data for each micro area of the two-dimensional area as shown in FIG. 3(b). The data processing unit also converts the time-of-flight into a mass axis to determine the intensity data with respect to each mass. Thus, mass spectrum data are obtained. These data are then plotted on a graph with m/z on the horizontal axis and the (relative) intensity of the ions on the vertical axis to obtain a mass spectrum.

In any of the mass spectrometers shown in FIGS. 1 and 2, mass spectrum data are obtained for each micro area within a predetermined two-dimensional area of the sample S. The mass spectrum data are temporarily stored in a hard disk or similar memory device in the data processing unit 8 or 15. Subsequently, as will be described later, the substances contained in the sample S is identified by a data analyzing process performed by the data processing unit 8 or 15.

Figure 5:
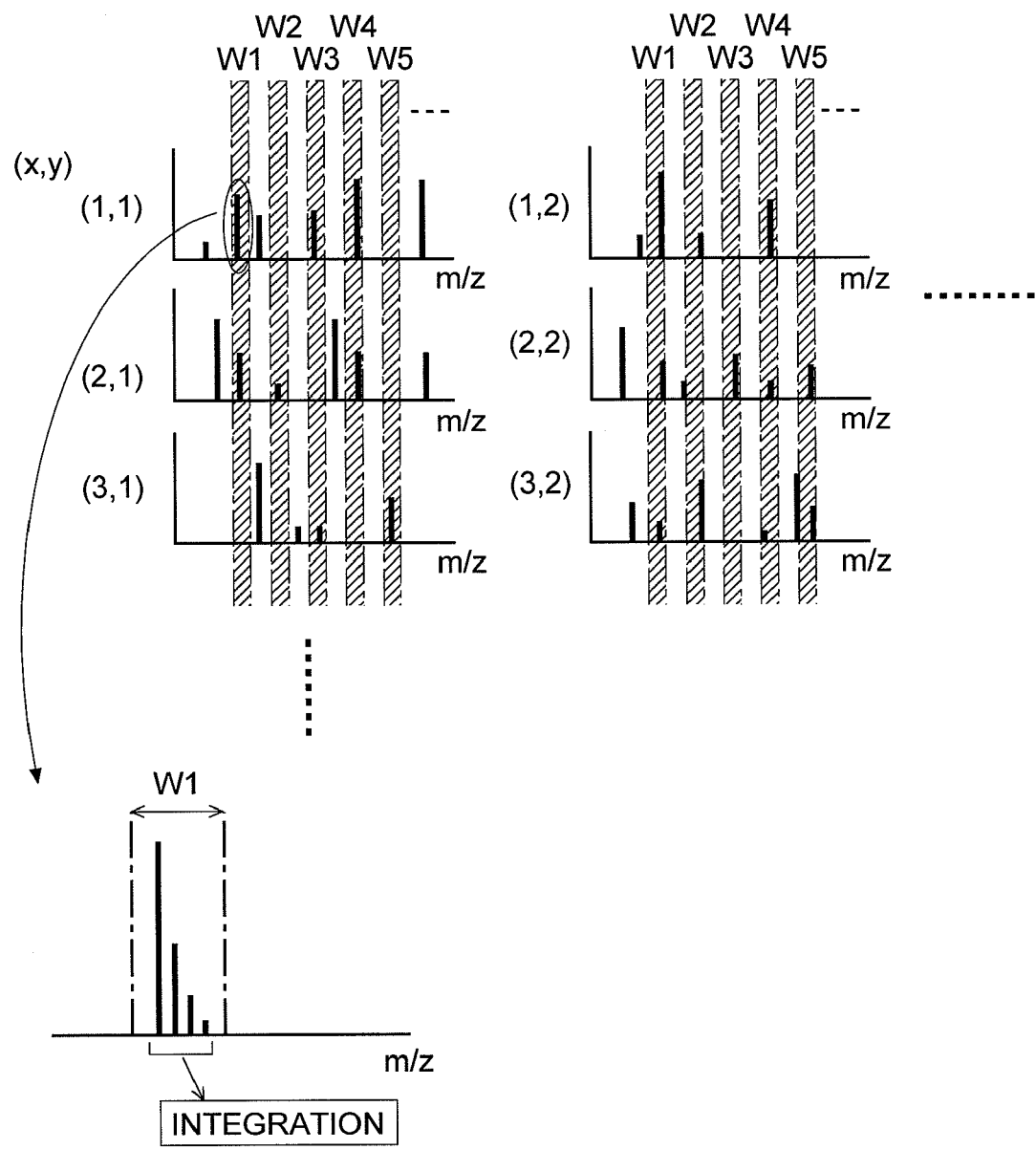
FIG. 5 is a model diagram for illustrating the steps of the mass spectrometry data analysis method according to the first embodiment.
Figure 6:
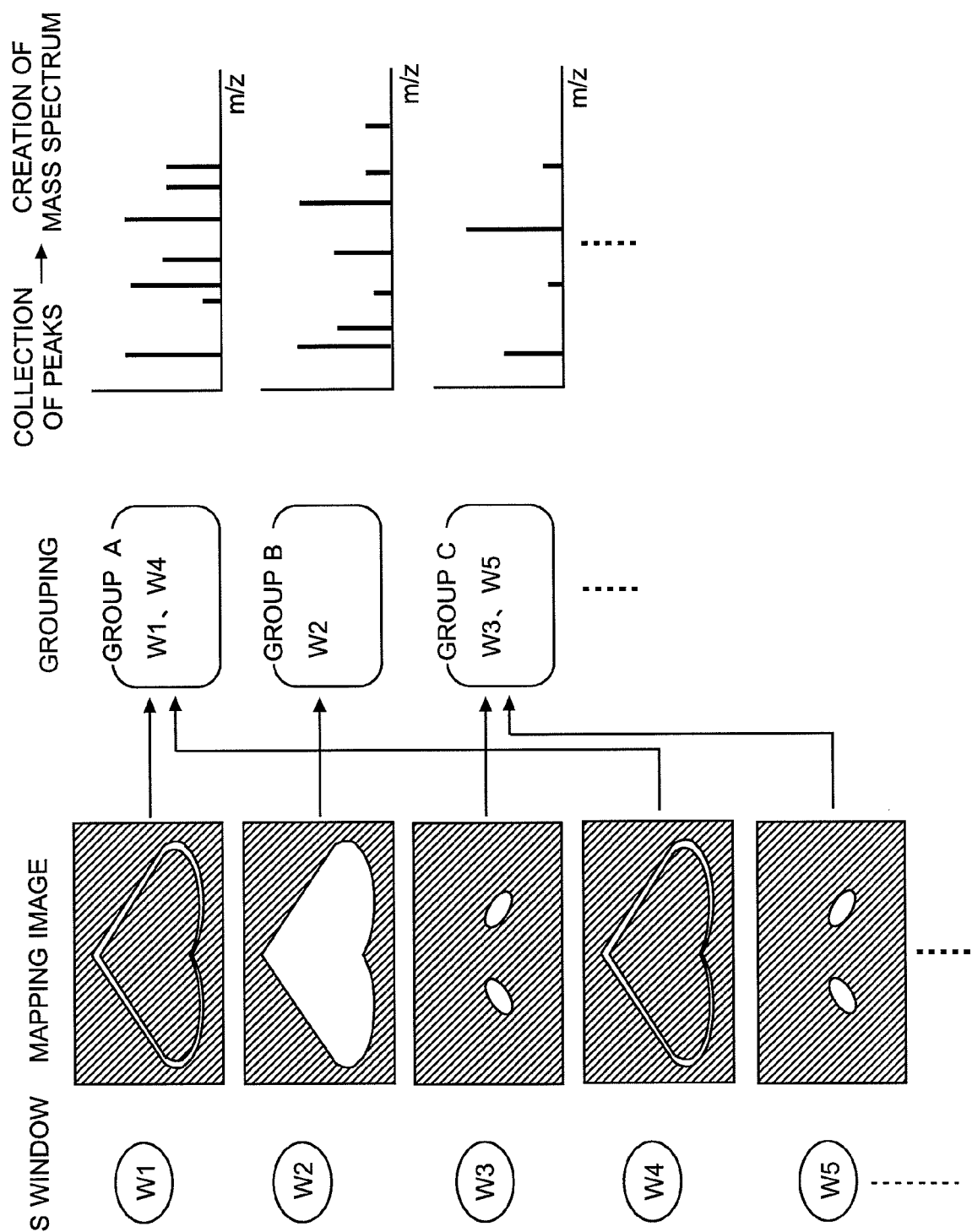
FIG. 6 is a model diagram for illustrating the steps of the mass spectrometry data analysis method according to the first embodiment.

A mass spectrometry data analysis method according to the first embodiment for analyzing mass spectrum data for each of the aforementioned micro areas is hereinafter described. FIG. 4 is a flowchart showing the process steps of the present mass spectrometry data analysis method, and FIGS. 5 and 6 are model diagrams for illustrating the operational steps of the analyzing process.

A sample that has been cut from a biological sample such as a mouse's brain is subjected to enzymatic digestion to break proteins into peptide fragments. With these fragments as the sample S to be analyzed, mass spectrum data are obtained with the previously described mass spectrometer. At this point, it is assumed that mass spectrums have been obtained for each pixel (or micro area) as shown in FIG. 5. In FIG. 5, (x, y) is an address assigned to each pixel on the X and Y axes, respectively, to represent the position of the pixel. The mass spectrum data forming these mass spectrums are given to the data processing unit 8 or 15, which performs an analyzing process to identify proteins.

First, a window with a predetermined mass width (mass window), which is common to all the pixels, is set for each peak on the mass spectrum (Step S10). In the example of FIG. 5, mass windows are set as indicated by W1, W2 and so on. At this stage, it is not necessary to set the mass windows so that they include the entire peaks. For example, it is possible to exclude peaks that have been unmistakably identified as noise peaks. The mass windows may be automatically set. Alternatively, an operator may appropriately set them by checking the position of each peak on a monitor's screen with the mass spectrum displayed as shown in FIG. 5. For the peaks of a peptide, there is normally an isotopic peak group. Therefore, it is desirable to set the mass windows so that a plurality of peaks that seem to belong to the same isotopic peak group will be included in one mass window.

Next, the ion intensities included in one mass window are integrated for each pixel (Step S11). For example, if there are a plurality of peaks within the mass window W1 at the pixel with an address of (1, 1) in FIG. 5, the ion intensities of those peaks are integrated, and the resulting value is selected as the integrated intensity value for that mass window.

After the integrated intensity value of each mass window has been calculated at the entire group of pixels included in the predetermined two-dimensional area as shown in FIG. 3(*b*), the integrated intensity values corresponding to the same mass window of the entire group of pixels are collected, and a mapping image is created using these integrated intensity values (Step S12). For example, collecting the integrated intensity values corresponding to the mass window W1 of the entire group of pixels will result in a mapping image as shown in FIG. 6. It is similarly assumed that collecting the integrated intensity values corresponding to each of the mass windows W2, W3 and so on results in a set of mapping images as shown in FIG. 6. That is, as many mapping images as the number of specified mass windows are created.

Subsequently, the correlation between the mapping images is evaluated in order to collect mapping images with similar image patterns (Step S13). For example, the degree of pattern matching is calculated for each pair of the mapping images, and the correlation is evaluated based on the degree of matching. Other kinds of techniques that are used for image recognition or other purposes may also be used to determine whether a given pair of images is similar or not.

Then, the entire set of mapping images are grouped in such a manner that any mapping images that are highly correlated (i.e. similar) to each other will belong to the same group (Step S14). In the example of FIG. 6, the mapping images corresponding to the mass windows W1 and W4 are similar to each other and therefore classified into the same group, labeled "A". Similarly, the mapping images corresponding to the mass windows W3 and W5 are similar to each other and classified into group C. Naturally, there may be a group that includes only one mapping image (e.g. group B in FIG. 6). Grouping the mapping images in this manner is equivalent to grouping the mass windows since each mapping image corresponds to one mass window.

As a result of this grouping operation, it is possible to assume that the peaks included in the mass windows belonging to the same group are the peaks of peptides originating from the same kind of protein. Accordingly, the peaks included in the mass windows belonging to the same group are collected for each group and then integrated to form a mass spectrum (Step S15). Thus, as many mass spectrums as the number of groups are created.

The previously described sequence of processes are performed to separate peaks for each kind of protein by using two-dimensional distribution information in the case where a plurality of peaks originating from two or more kinds of proteins are mixed together on a mass spectrum corresponding to each micro area. Therefore, it can be presumed that the mass spectrum created in Step S15 is composed of the peaks of peptides originating from one kind of protein. Based on this presumption, information (i.e. mass and peak intensity) of the peaks on each mass spectrum is used to identify a protein by a database search using a PMF method (Steps S16 and S17).

To identify a protein by using a mass spectrum that has been created for each group, there are various kinds of conventional methods available. For example, one method includes finding an isotopic peak group in the mass spectrum, locating a mono-isotopic ion among a plurality of peaks belonging to that isotopic peak group, and searching a database for the mass of the mono-isotopic ion. This database search may alternatively use an average value of the masses of a plurality of peaks belonging to the isotopic peak group.

In the case of using a mass spectrometer capable of MS/MS analysis, it is possible to perform an MS/MS analysis with an isotopic peak group (or a portion of the group in some cases) as a precursor ion, then deduce an amino acid sequence from the masses of the peaks located on a resultant mass spectrum (MS/MS spectrum), and eventually identify the protein.

Figure 9:
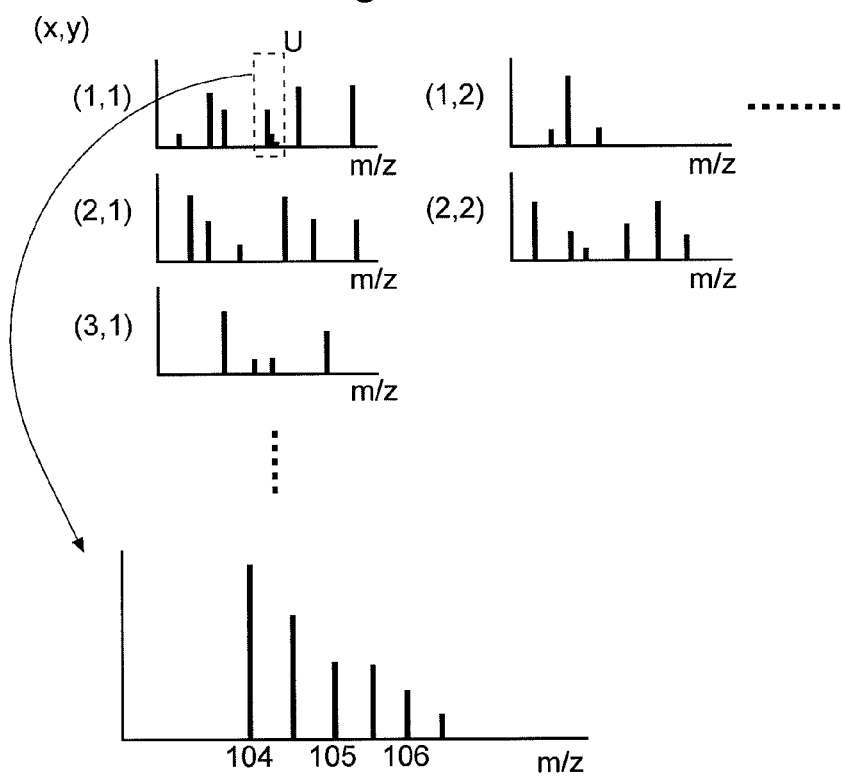
FIG. 9 is a model diagram for illustrating the steps of the mass spectrometry data analysis method according to the second embodiment.
Figure 10:
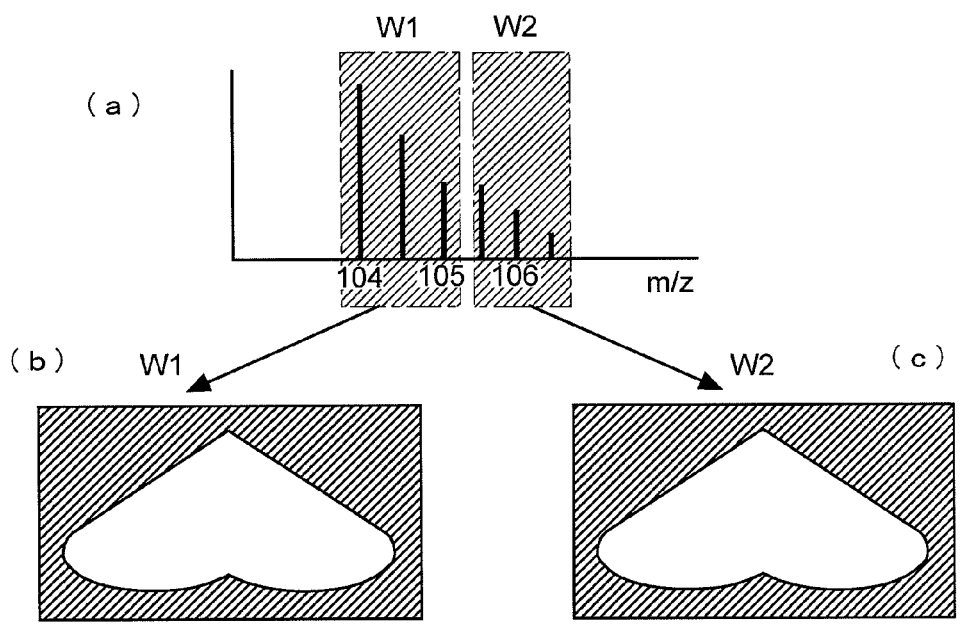
FIG. 10 is a model diagram for illustrating the steps of the mass spectrometry data analysis method according to the second embodiment.
Figure 11:
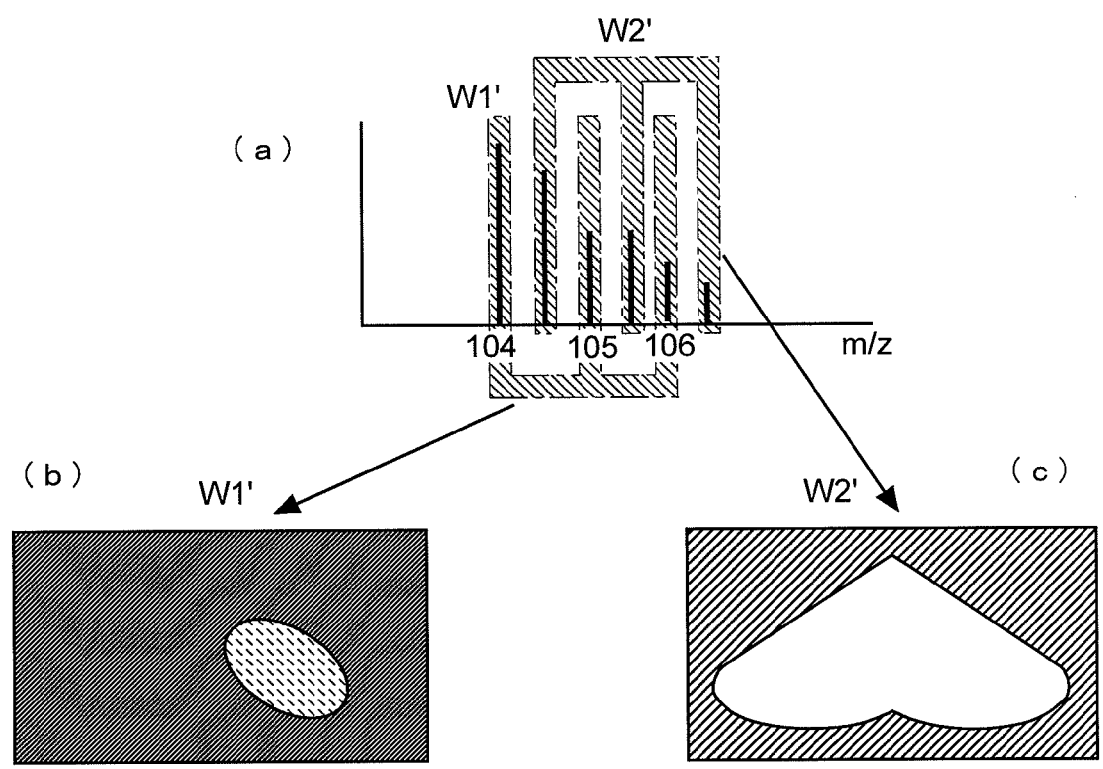
FIG. 11 is a model diagram for illustrating the steps of the mass spectrometry data analysis method according to the second embodiment.

A mass spectrometry data analysis method according to the second embodiment for analyzing mass spectrum data for each of the aforementioned micro areas is hereinafter described. FIG. 7 is a flowchart showing the process steps of the present mass spectrometry data analysis method. FIG. 8 shows an observed image of one example of the sample to be analyzed. FIGS. 9, 10 and 11 are model diagrams for illustrating the operational steps of the analyzing process.

The following description deals with a case as shown in FIG. 8, where the sample to be analyzed includes a pathological tissue Q (e.g. a cancer) within a normal tissue P. In most cases, a pathological tissue Q can be roughly distinguished from the normal tissue P by visual observation of the sample with a microscope or imaging device. Therefore, in performing a mass analysis on a predetermined two-dimensional area, it is possible to roughly determine which pixels correspond to the pathological tissue Q.

A sample as shown in FIG. 8 is then subjected to enzymatic digestion to break proteins into peptide fragments. Using these fragments as the sample S to be analyzed, mass spectrum data are obtained by a previously described mass spectrometer. At this point, it is assumed that mass spectrums have been obtained at each pixel as shown in FIG. 9. From these mass spectrums, a superposed isotopic peak group, which is presumed to be a mixture of isotopic peaks originating from two or more kinds of proteins, is extracted (Step S20). At this point, it is assumed that the peak U in the mass spectrum corresponding to the pixel with an address of (1, 1) in FIG. 9 is a superposed isotopic peak group having six peaks.

Next, a theoretical peak intensity ratio of the peaks belonging to the isotopic peak group of the substance (peptide) corresponding to the mass of the aforementioned superposed isotopic peak group is calculated (Step S21). At this point, it is assumed that there are three peaks with a peak intensity ratio of 100:70:40. With reference to this peak intensity ratio, an attempt is made to divide the six peaks belonging to the superposed isotopic peak group into two subgroups. There are two possible combinations as the candidates. According to the first combination, the peaks are divided into three foregoing peaks and three following peaks, with each subgroup forming an isotopic peak group as shown in FIG. 10(a). (This corresponds to the case of bivalent ions.) According to the second combination, the peaks are divided into two sets of three peaks by selecting every other peak, with each subgroup forming an isotopic peak group as shown in FIG. 11(a). (This corresponds to the case of monovalent ions.) Accordingly, as shown in FIGS. 10(a) and 11(a), mass windows W1 and W2 or W1' and W2' for dividing the superposed isotopic peak group into two isotopic peak groups are set for each candidate (Step S22).

Subsequently, for each of the aforementioned two candidate combinations for dividing the isotopic peak groups, the ion intensities included in one of the mass windows W1 and W2 (or W1' and W2') are integrated for each pixel (Step S23). For example, when the mass windows W1 and W2 are set as shown in FIG. 10(a), the ion intensities of one or more peaks located within a mass range from 103.5 to 105.5 at each pixel are integrated, and the resultant value is selected as the integrated intensity value for the mass window W1. Similarly, the ion intensities of one or more peaks located within a mass range from 105.5 to 107.5 at each pixel are integrated, and the resultant value is selected as the integrated intensity value for the mass window W2.

After the integrated intensity value for each of the mass windows W1 and W2 (or W1' and W2') has been calculated at the entire group of pixels included in the predetermined two-dimensional area, the integrated intensity values corresponding to the same mass window of the entire group of pixels are collected, and a mapping image is created from these integrated intensity values (Step S24). For example, collecting the integrated intensity values corresponding to the mass window W1 of the entire group of pixels will result in a mapping image as shown in FIG. 10(b). Similarly, collecting the integrated intensity values corresponding to the mass window W2 will result in a mapping image as shown in FIG. 10(c). On the other hand, collecting the integrated intensity values corresponding to the mass window W1' of the entire group of pixels will result in a mapping image as shown in FIG. 11(b). Similarly, collecting the integrated intensity values corresponding to the mass window W2' will result in a mapping image as shown in FIG. 11(c).

Next, the mapping images created in the preceding step are evaluated (Step S25). In the present example, each set of the resultant mapping images is evaluated by checking whether or not those mapping images correspond to the normal tissue P and pathological tissue Q that can be distinguished on a visually observed image. In the case of FIGS. 10(b) and 10(c), both mapping images correspond to the normal tissue P; none of them corresponds to the pathological tissue Q. In the case of FIGS. 11(b) and 11(c), the resultant mapping images respectively correspond to the normal tissue P and pathological tissue Q. Therefore, it is possible to conclude that the peak selection method shown in FIG. 11(a) should be used to divide the superposed isotopic peak group into two isotopic peak groups. After the isotopic peak groups are thus established (Step S26), it is possible to consider that one isotopic peak group corresponds to the normal tissue P and the other isotopic peak group to the pathological tissue Q.

Accordingly, a monoisotopic peak is located among the isotopic peak groups (Step S27), and a protein is identified from the mass of the monoisotopic peak (Step S28). In the example of FIG. 11, the monoisotopic peak of the isotopic peak group characteristic of the pathological tissue Q has a m/z value of 104 (valence+1). This information can be used in a database search to identify a protein contained in the pathological tissue Q.

In the case of using a mass spectrometer capable of MS/MS analysis, after an isotopic peak group corresponding to a pathological tissue has been located in the previously described manner, it is possible to perform an MS/MS analysis with this isotopic peak group (or a portion of the group in some cases) as a precursor ion, then deduce an amino acid sequence from the masses of the peaks located on a resultant mass spectrum (MS/MS spectrum), and eventually identify the protein.

After the substance is identified in the previously described manner, it is possible to additionally determine the quantity of the substance by calculating the total amount of the ions originating from this substance across the entire two-dimensional area.

The previously described process of analyzing mass spectrum data for identifying proteins or other substances can be practically realized by executing a dedicated software program on a general-purpose computer.

It should be notated that the previous embodiments are mere examples of the present invention; it is evident that any change, modification or addition appropriately made within the spirit of the present invention will be included in the scope of the claims of the present patent application.

The invention claimed is:

1. A mass spectrometry data analysis method for analyzing and processing mass spectrum data collected by a mass analysis performed for each of micro areas defined within a predetermined two-dimensional area on a sample, which is characterized by comprising a distinguishing step for distinguishing a peak or peak set originating from one kind of substance from a peak or peak set originating from another kind of substance, using a two-dimensional distribution of a peak having a same mass and appearing on mass spectrums corresponding to a portion or the entirety of the micro areas or a peak set composed of one or more peaks included in a same mass range on the mass spectrums.

2. A mass spectrometry data analysis method for analyzing and processing mass spectrum data collected by performing a mass analysis for each of micro areas defined within a predetermined two-dimensional area on a sample, which is characterized by comprising:

a) a distribution determining step for determining a two-dimensional distribution of each peak having a same mass and appearing on mass spectrums corresponding to a portion or the entirety of the micro areas or each peak set composed of one or more peaks included in a same mass range on the mass spectrums;

b) a grouping step for separating the peaks or peak sets into one or more groups based on a degree of similarity of the two-dimensional distribution; and c) a spectrum creating step for creating a mass spectrum for each group from the peaks or peak sets separated into the group, and an identification process is performed on an assumption that the mass spectrum created in the spectrum creating step has originated from a same substance.

3. The mass spectrometry data analysis method according to claim 2, which is characterized in that:

the distribution determining step includes creating a mapping image showing the two-dimensional distribution of a peak having a same mass or a peak set composed of one or more peaks included in a same mass range; and the grouping step includes performing the grouping of mapping images by checking a similarity of the mapping images.

4. A mass spectrometry data analysis system for analyzing and processing mass spectrum data collected by performing a mass analysis for each of micro areas defined within a predetermined two-dimensional area on a sample, which is characterized by comprising:

a) a distribution determining means for determining a two-dimensional distribution of each peak having a same mass and appearing on mass spectrums corresponding to a portion or the entirety of the micro areas or each peak set composed of one or more peaks included in a same mass range on the mass spectrums;

b) a grouping means for separating the peaks or peak sets into one or more groups based on a degree of similarity of the two-dimensional distribution;

c) a spectrum creating means for creating a mass spectrum for each group from the peaks or peak sets classified into the group; and d) an identifying means for performing an identification process on an assumption that the mass spectrum created by the spectrum creating means has originated from a same substance.

5. The mass spectrometry data analysis system according to claim 4, which is characterized in that:

the distribution determining means creates a mapping image showing the two-dimensional distribution of a peak having a same mass or a peak set composed of one or more peaks included in a same mass range; and the grouping means performs the grouping of mapping images by checking a similarity of the mapping images.

6. A mass spectrometry data analysis method for analyzing and processing mass spectrum data collected by performing a mass analysis for each of micro areas defined within a predetermined two-dimensional area on a sample, which is characterized by comprising:

a) an isotopic group extracting step for extracting a superposed isotopic peak group formed by a plurality of isotopic peak groups originating from two or more kinds of substances and superposed on each other on a mass spectrum corresponding to one of the micro areas;

b) a separation candidate calculating step for finding a candidate combination of the peaks for separating the superposed isotopic peak group into individual isotopic peak groups each originating from one kind of substance, by using a theoretical peak intensity ratio deduced from a mass of a specific peak selected from a plurality of peaks composing the superposed isotopic peak group;

c) a distribution determining step for setting a mass range including a peak belonging to an isotopic peak group for each candidate combination of the peaks, and for determining a two-dimensional distribution of each peak set composed of one or more peaks included in the aforementioned mass range and appearing on mass spectrums corresponding to a portion or the entirety of the micro areas; and d) an isotopic peak group separating step for separating the superposed isotopic peak group into individual isotopic peak groups by selecting one candidate of the peak combination on a basis of the aforementioned two-dimensional distribution.

7. A mass spectrometry data analysis system for analyzing and processing mass spectrum data collected by performing a mass analysis for each of micro areas defined within a predetermined two-dimensional area on a sample, which is characterized by comprising:

a) an isotopic group extracting means for extracting a superposed isotopic peak group formed by a plurality of isotopic peak groups originating from two or more kinds of substances and superposed on each other on a mass spectrum corresponding to one of the micro areas;

b) a separation candidate calculating means for finding a candidate combination of the peaks for separating the superposed isotopic peak group into individual isotopic peak groups each originating from one kind of substance, by using a theoretical peak intensity ratio deduced from a mass of a specific peak selected from a plurality of peaks composing the superposed isotopic peak group;

c) a distribution determining means for setting a mass range including a peak belonging to an isotopic peak group for each candidate combination of the peaks, and for determining a two-dimensional distribution of each peak set composed of one or more peaks included in the aforementioned mass range and appearing on mass spectrums corresponding to a portion or the entirety of the micro areas; and d) an isotopic peak group separating step for separating the superposed isotopic peak group into individual isotopic peak groups by selecting one candidate of the peak combination on a basis of the aforementioned two-dimensional distribution.

* * * * *